United States Patent [19]

Ishizumi et al.

[11] Patent Number: 4,610,986
[45] Date of Patent: Sep. 9, 1986

[54] AMINONAPHTHACENE DERIVATIVES AND THEIR PRODUCTION

[75] Inventors: Kikuo Ishizumi, Toyonaka; Michihisa Muramatsu, Osaka; Norihiko Tanno, Ibaragi; Hiromi Sato, Toyonaka; Noboru Yoshida, Osaka, all of Japan

[73] Assignee: Sumitomo Chemical Company, Limited, Osaka, Japan

[21] Appl. No.: 660,039

[22] Filed: Oct. 12, 1984

Related U.S. Application Data

[63] Continuation-in-part of Ser. No. 397,787, Jul. 13, 1982, abandoned.

[30] Foreign Application Priority Data

Jul. 29, 1981 [JP] Japan .................... 56-119949
Jan. 27, 1982 [JP] Japan .................... 57-12134
May 11, 1982 [JP] Japan .................... 57-79525

[51] Int. Cl.[4] .................... A01N 43/84; C07C 50/16; C07C 97/26; C07C 49/68
[52] U.S. Cl. .................... 514/239; 260/365; 260/376; 260/380; 260/351.1; 514/227; 514/280; 514/282; 514/463; 514/325; 514/680; 544/154; 544/380; 544/381; 549/451
[58] Field of Search .......... 260/365, 376, 380, 351.1; 549/451; 544/381, 380, 154; 514/680, 325, 239, 227, 280, 282, 463

[56] References Cited

U.S. PATENT DOCUMENTS 3,665,018 5/1972 Jolles .................... 260/365
3,963,760 6/1976 Bernardi et al. .................... 260/365
4,077,988 3/1978 Arcamone et al. .................... 260/365
4,089,872 5/1978 Koert et al. .................... 260/365

FOREIGN PATENT DOCUMENTS 887081 5/1981 Belgium .................... 514/680

OTHER PUBLICATIONS

Acton et al, *J. Med. Chem.*, vol. 22, No. 8, pp. 922-926 (1979).
Gssery et al, *J. Med. Chem.*, vol. 22, No. 11, pp. 1425-1428 (1979).
Inaba et al, *Cancer Research*, vol. 39, pp. 2200-2203 (Jun. 1979).

*Primary Examiner*—Glennon H. Hollrah
*Assistant Examiner*—Raymond Covington
*Attorney, Agent, or Firm*—Birch, Stewart, Kolasch & Birch

[57] ABSTRACT

A (7S,9S) isomer or its racemic modification of the aminonaphthacene derivative of the formula:

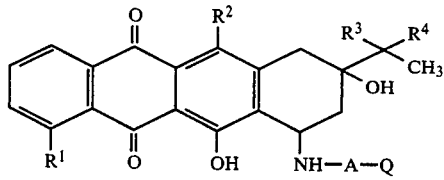

wherein $R^1$ is a hydrogen atom, a hydroxyl group or a lower alkoxy group, $R^2$ is a hydrogen atom or a hydroxyl group, $R^3$ and $R^4$ are each a lower alkoxy group or, when taken together, represent an ethylenedioxy group or an oxo group, A is an ethylene group optionally bearing at least one lower alkyl and Q is a hydroxyl group, a lower alkoxy group or a dimethylamino group, or an acid addition salt thereof, which is useful as an anti-tumor agent.

10 Claims, No Drawings

AMINONAPHTHACENE DERIVATIVES AND THEIR PRODUCTION

This is a continuation-in-part application of our co-pending application Ser. No. 397,787 filed July 13, 1982 now abandoned.

The present invention relates to aminonaphthacene derivatives and their production.

The aminonaphthacene derivatives are representable by the formula:

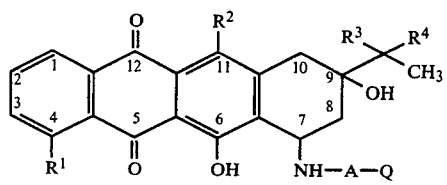

(I)

wherein $R^1$ is a hydrogen atom, a hydroxyl group or a lower alkoxy group, $R^2$ is a hydrogen atom or a hydroxyl group, $R^3$ and $R^4$ are each a lower alkoxy group or, when taken together, represent an ethylenedioxy group or an oxo group, A is an ethylene group optionally bearing at least one lower alkyl and Q is a hydroxyl group, a lower alkoxy group or a dimethylamino group, or an acid addition salt thereof.

In the foregoing and subsequent significances, the term "lower alkyl" means straight or branched alkyl having not more than 4 carbon atoms and includes methyl, ethyl, n-propyl, isopropyl, n-butyl, isobutyl, t-butyl, etc. The term "lower alkoxy" means straight or branched alkyl having not more than 4 carbon atoms and includes methoxy, ethoxy, n-propoxy, isopropoxy, n-butoxy, isobutoxy, t-butoxy, etc.

The aminonaphthacene derivatives (I) have two asymmetric atoms, i.e. at the 7- and 9-positions, and are therefore intended to include the following four isomers:

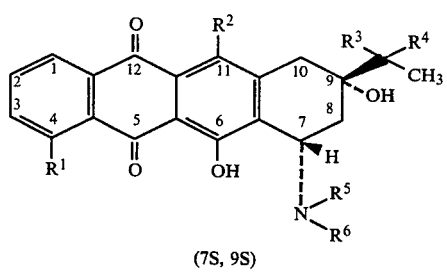

(7S, 9S)

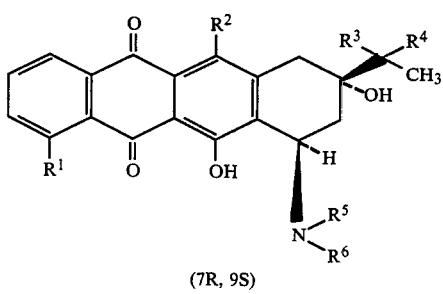

(7R, 9S)

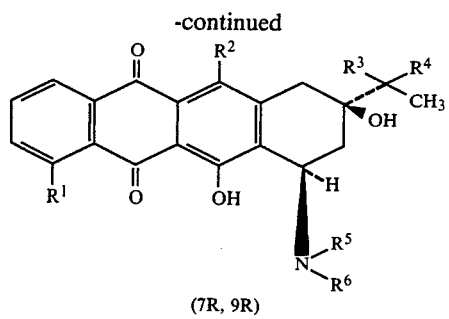

(7R, 9R)

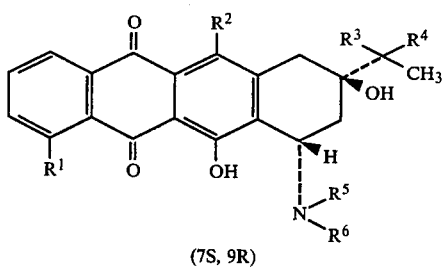

(7S, 9R)

among which the (7S,9S) isomer is the most preferred.

Hitherto, there are known some anthracyclines which are useful as anti-tumor agents. Particularly, adriamycin (hereinafter referred to as "ADR") and daunomycin (hereinafter referred to as "DMC") show a strong anti-tumor activity and are clinically used. However, they produce remarkable side effects including cardiac toxicity. In addition, their separation and purification from natural sources are difficult and troublesome.

Recently, chemical modification of ADR and DMC as well as total synthesis of their analogous compounds has been attempted. In particular, many studies have been made on the replacement of the sugar portion of ADR and DMC by any other organic group, and a great number of compounds have been provided. However, none of them has been reported to exert a signiticant anti-tumor activity. For instance, 7-O-beta-alanine ester and 7-O-beta-aminoethyl ether of duanomycinone show only an uncertain effect against P388 leukemia in the animal test using mice (J. Med. Chem., 22, 922–926).

It has now been unexpectedly found that the aminonaphthacene derivatives (I), particularly their (7S,9S) isomer and racemic modifications thereof, show a remarkable anti-tumor activity. For instance, they produce a significant growth inhibition against P388 tumor cells in the in vitro test as shown in Table 1. Further, for instance, they produce a notable prolongation of life in the test using mice transplanted with P388 tumor cells.

TABLE 1

| Test Compound | Concentration (μ/ml) | Inhibition (%) |
|---|---|---|
| 7-(2-Hydroxyethyl)amino-9-acetyl 6,9,11-trihydroxy-5,7,8,9,10,12-hexahydronaphthacene-5,12-dione | 1 | 76.4 |
| 7-(2-Dimethylaminoethyl)amino-9-(1-ethylenedioxy)ethyl-6,9,11-trihydroxy-5,7,8,9,10,12-hexahydronaphthacene-5,12-dione | 1 | 72.1 |
| 7-(2-Dimethylaminoethyl)amino-9-acetyl-6,9,11-trihydroxy-5,7,8,9,10,12-hexahydronaphthacene-5,12-dione | 1 | 77.7 |
| 7(S)—(2-Dimethylaminoethyl)amino- | 1 | 71.2 |

TABLE 1-continued

| Test Compound | Concentration (μ/ml) | Inhibition (%) |
| --- | --- | --- |
| 9(S)—acetyl-6,9,11-trihydroxy-5,7,8,9,10,12-hexahydronaphthacene-5,12-dione | | |
| 7(S)—(2-Dimethylaminoethyl) amino-7-deoxydaunomycinone | 1 | 69.0 |
| Daunomycin | 1 | 68.3 |

Thus, the aminonaphthacene derivatives (I) are characteristic in having the structure comprising an anthracycline aglycon and an amino group introduced into the 7-position of the aglycon and yet showing a significant anti-tumor activity.

The aminonaphthacene derivatives (I) are useful as anti-tumor agents. They can be administered parenterally, orally or locally to warm-blooded animals and human beings in the form of conventional pharmaceutical preparations. For instance, they can be administered in the form of conventional solid pharmaceutical preparations such as tablets, capsules, powders or granules, or in the form of conventional liquid pharmaceutical preparations such as suspensions, emulsions or solutions. The daily dosage may vary depending upon the administration route and is usually between 0.1 to 100 mg/kg.

The aminonaphthacene derivatives (I), i.e. the 7-amino compounds, can be produced from the corresponding 7-H compound of the formula:

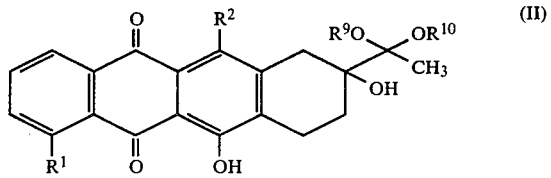

wherein $R^9$ and $R^{10}$ are each a lower alkyl group or, when taken together, represent an ethylene group and $R^1$ and $R^2$ are each as defined above by reacting the same with a halogenating agent to give the 7-X compound of the formula:

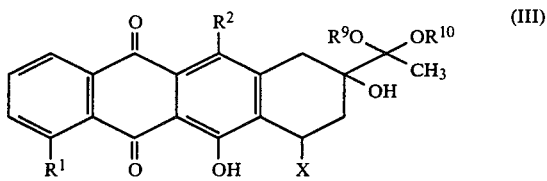

wherein X is a halogen atom (e.g. fluorine, chlorine, bromine, iodine) and $R^1$, $R^2$, $R^9$ and $R^{10}$ are each as defined above and reacting the latter with an amrne of the formula:

$$HN_2-A-Q \qquad (C)$$

wherein A and Q are each as defined above to give the 7-amino compound of the formula:

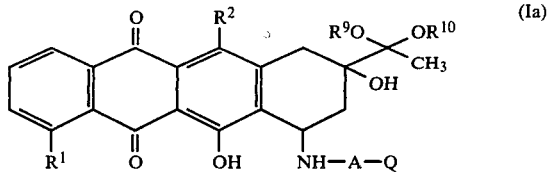

wherein $R^1$, $R^2$, $R^9$, $R^{10}$, A and Q are each as defined above, optionally followed by elimination of the acetal group at the 13-position to give the 7-amino compound of the formula:

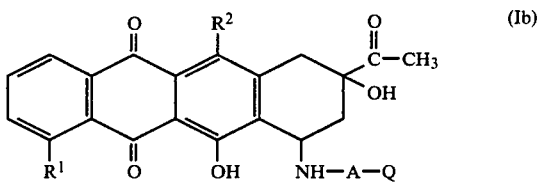

wherein $R^1$, $R^2$, A and Q are each as defined above.

The starting 7-H compound is per se known and can be produced by subjecting the corresponding 9-acetyl compound to acetalation by a conventional procedure.

The reaction of the 7-H compound (II) with a halogenating agent proceeds usually at a temperature of not lower than room temperature and can be accelerated by heating. When desired, a radical initiator (e.g. azobisisobutyronitrile, benzoyl peroxide) may be incorporated into the reaction system or a visible ray may be irradiated to the reaction system, whereby the reaction is promoted. Examples of the halogenating agent are bromine, chlorine, N-bromosuccinimide, N-chlorosuccinimide, etc. The reaction is normally effected in an inert solvent such as a halogenated hydrocarbon (e.g. carbon tetrachloride, chloroform, dichloromethane), an aromatic hydrocarbon (e.g. benzene, toluene), an aliphatic hydrocarbon (e.g. n-hexane, cyclohexane), an ether (e.g. diethyl ether, tetrahydrofuran, dioxane, diglyme), an amide (e.g. dimethylformamide), acetic acid or water, etc.

The reaction of the 7-X compound (III) with the amine (C) proceeds normally at room temperature but may be accelerated by heating. The reaction is usually carried out in an inert solvent such as an aromatic hydrocarbon (e.g. benzene, toluene), an ether (e.g. dimethyl ether, tetrahydrofuran), a halogenated hydrocarbon (e.g. carbon tetrachloride, chloroform, dichloromethane), an aliphatic hydrocarbon (e.g. n-hexane, cyclohexane) or an amide (e.g. dimethylformamide). When the amine (C) is a liquid at room temperature, it may be used as such as the reaction medium. In such case, the use of any other solvent is not necessarily needed.

Elimination of the acetal group at the 13-position as the optional step may be carried out by a per se conventional procedure such as hydrolysis under an acidic or basic condition or exchange in acetone under an acidic condition.

The thus produced amino compound (Ia) or (Ib) can be converted into its acid addition salt by treatment with an organic or inorganic acid. The control of the amount of the organic or inorganic acid to be used gives the salts in various molar proportions of the amino compound (Ia) or (Ib) and the organic or inorganic acid. Examples of the organic or inorganic acid are hydrochloric acid, hydrobromic acid, malic acid, citric acid, tartaric acid, etc.

Among the aminonaphthacene derivatives (I), their (7S,9S) isomers and racemic modifications thereof are preferred. Particularly preferred are the (7S,9S) isomer or its racemic modification of 7-(2-dimethylaminoethyl)amino-9-acetyl-6,9,11-trihydroxy-5,7,8,9,10,12-hexahydronaphthacene-5,12-dione, the (7S,9S) isomer or its racemic modification of 7-(2-hydroxyethyl)amino-9-acetyl-6,9,11-trihydroxy-5,7,8,9,10,12-hexahydronaphthacene-5,12-dione, the (7S,9S) isomer or its racemic modification of 7-(2-methoxyethyl)amino-9-acetyl-6,9,11-trihydroxy-5,7,8,9,10,12-hexahydronaphthacene-5,12-dione, the (7S,9S) isomer or its racemic modification of 7-(2-hydroxypropyl)amino-9-acetyl-6,9,11-trihydroxy-5,7,8,9,10,12-hexahydronaphthacene-5,12-dione, etc.

Practical and presently preferred embodiments of the invention are illustratively shown in the following examples.

EXAMPLE 1

(1) 9-(1,1-Ethylenedioxy)ethyl-6,9,11-trihydroxy-5,7,8,9,10,12-hexahydronaphthacene-5,12-dione (10.0 g) was dissolved in a mixture of chloroform (395 ml), carbon tetrachloride (980 ml) and water (890 ml) while heating, azobisisobutyronitrile (2.0 g) and bromine (8.0 g) were added thereto in order, and the resultant mixture was stirred under reflux for 1.5 hours. The reaction mixture was stirred in an ice bath for 1 hour, and the precipitated red orange crystals were collected by filtration, washed with water and dried under reduced pressure to give the crude product of 7-bromo-9-(1,1-ethylenedioxy)ethyl-6,9,11-trihydroxy-5,7,8,9,10,12-hexahydronaphthacene-5,12-dione. M.P., 196°–235° C.; IR (Nujol) $\nu$ cm$^{-1}$: 3550, 1625, 1590. This product was used as such in the following step without purification.

(2) 7-Bromo-9-(1,1-ethylenedioxy)ethyl-6,9,11-trihydroxy-5,7,8,9,10,12-hexahydronaphthacene-5,12-dione (1.0 g) prepared in the foregoing step and N,N-dimethylethylenediamine (10 ml) were subjected to reaction at room temperature in a nitrogen stream for 48 hours. N,N-Dimethylethylenediamine was removed by distillation under reduced pressure. The residue was dissolved in water (5 ml), adjusted to pH 8 with aqueous hydrochloric acid and extracted with chloroform. The chloroform extract was washed with water, dried over anhydrous sodium sulfate and concentrated. The resultant crude product was purified by silica gel chromatography using a mixture of chloroform and methanol (9:1) as an eluting solvent to give 7-(2-dimethylaminoethyl)amino-9-(1,1-ethylenedroxy)ethyl-6,9,11-trihydroxy-5,7,8,9,10,12-hexahydronaphthacene-5,12-dione as orange crystals. M.P., 239°–244° C.

IR (Nujol) $\nu$ cm$^{-1}$: 1630, 1595. NMR (CDCl$_3$) $\delta$: 1.5 (3H, s), 2.25 (6H, s), 2.0–3.15 (8H, m), 4.05 (4H, s), 4.17–4.33 (1H, bs), 7.65–7.90 (2H, m), 8.06–8.37 (2H, m). Mass spectrum (by the field desorption mass spectrometry): 483 (M+1)$^+$.

EXAMPLE 2

In the same manner as in Example 1 (2), 7-bromo-9-(1,1-ethylenedioxy)ethyl-6,9,11-trihydroxy-5,7,8,9,10,12-hexahydronaphthacene-5,12-dione (1.0 g) prepared in Example 1 (1) and N,N-dimethylethylenediamine (10 ml) were subjected to reaction. After removal of excessive N,N-dimethylethylenediamine by distillation under reduced pressure, the residue was crystallized from dichloromethane and ether to give 7-(2-dimethylaminoethyl)amino-9-(1,1-ethylenedioxy)ethyl-6,9-11-trihydroxy-5,7,8,9,10,12-hexahydronaphthacene-5,12-dione as orange crystals. M.P., 242°–245° C.

EXAMPLE 3

7-(2-(Dimethylaminoethyl)amino-9-(1,1-ethylenedioxy)ethyl-6,9,11-trihydroxy-5,7,8,9,10,12-hexahydronaphthacene-5,12-dione (900 mg) prepared in Example 1 (2) was added to a mixture of acetone (90 ml) and conc. hydrochloric acid (36 ml), and the resultant mixture was heated at 50° to 60° C. for 6 hours. After removal of acetone by distillation under reduced pressure, the residue was adjusted to pH 8.0 with aqueous sodium hydroxide solution and extracted with chloroform. The chloroform extract was purified by silica gel chromatography using a mixture of chloroform and methanol (9:1) as an eluting solvent to give 7-(2-dimethylaminoethyl)amino-9-acetyl-6,9,11-trihydroxy-5,7,8,9,10,12-hexahydronaphthacene-5,12-dione as orange crystals. M.P., 147° C. (decomp.).

IR (Nujol) $\nu$ cm$^{-1}$: 3330, 1720, 1630, 1590. NMR (CDCl$_3$) $\delta$: 1.10–1.90 (2H, m), 2.00–3.55 (8H, m), 2.23 (6H, s), 2.40 (3H, s), 4.30 (1H, bs), 7.65–7.95 (2H, m), 8.10–8.40 (2H, m). Mass spectrum: 440 (M+1)$^+$.

EXAMPLE 4

In the same manner as in Example 1 (2), 7-bromo-9-(1,1-ethylenedioxy)ethyl-6,9,11-trihydroxy-5,7,8,9,10,12-hexahydronaphthacene-5,12-dione (1.0 g) prepared in Example 1 (1) and ethanolamine (20 ml) were subjected to reaction to give 7-(2-hydroxyethyl)amino-9-(1,1-ethylenedioxy)ethyl-6,9,11-trihydroxy-5,7,8,9,10,12-hexahydronaphthacene-5,12-dione as orange crystals. M.P., 190° C. (decomp.).

IR (Nujol) $\nu$ cm$^{-1}$: 3530, 3330, 1630, 1590. NMR (CDCl$_3$) $\delta$: 1.43 (3H, s), 2.24–4.15 (8H, m), 4.03 (4H, s), 4.24–4.35 (1H, bs) 7.55–7.85 (2H, m), 7.9–8.2 (2H, m). Mass spectrum: 456 (M+1)$^+$.

EXAMPLE 5

In the same manner as in Example 1 (2), 7-bromo-9-(1,1-ethylenedioxy)ethyl-6,9,11-trihydroxy-5,7,8,9,10,12-hexahydronaphthacene-5,12-dione prepared in Example 1 (1) and 2-hydroxypropylamine were subjected to reaction to give 7-(2-hydroxyethyl)amino-9-acetyl-6,9,11-trihydroxy-5,7,8,9,10,12-hexahydronaphthacene-5,12-dione. M.P., 157°–158° C.

IR (Nujol) $\nu$ cm$^{-1}$: 3300, 1710, 1620, 1590. NMR (CDCl$_3$) $\delta$: 1.17–1.37 (3H, m), 1.68 (1H, dd), 2.13 (1H, d), 2.43 (3H, s), 2.50–3.10 (4H, m), 4.15 (1H, bs), 7.60–7.87 (2H, m), 7.70–8.20 (2H, m). Mass spectrum: 425 M$^+$.

Hydrochloride, M.P., 147°–150° C.

EXAMPLE 6

In the same manner as in Example 3, 7-(2-hydroxyethyl)amino-9-(1,1-ethylenedioxy)ethyl-6,9,11-trihydroxy-5,7,8,9,10,12-hexahydronaphthacene-5,12-dione (1.0 g) prepared in Example 4 was subjected to reaction and post-treatment to give 7-(2-hydroxyethyl)amino-9-acetyl-6,9,11-trihydroxy-5,7,8,9,10,12-hexahydronaphthacene-5,12-dione. M.P., 125°–130° C.

IR (Nujol) $\nu$ cm$^{-1}$: 3400, 3300, 1705, 1620, 1590. NMR (CDCl$_3$) $\delta$: 1.65–2.25 (2H, m), 2.45 (3H, s), 2.90–3.15 (4H, m), 3.60–4.12 (2H, m), 4.30–4.45 (1H, bs), 7.75–7.82 (2H, m), 8.16–8.36 (2H, m).

EXAMPLE 7

(1) 9(R)-(1,1-Ethylenedioxy)ethyl-6,9,11-trihydroxy-5,7,8,9,10,12-hexahydronaphthacene-5,12-dione (1.35 g) produced from 9(R)-acetyl-6,9,11-trihydroxy-5,7,8,9,10,12-hexahydronaphthacene-5,12-dione ($[\alpha]_D^{20} -87°$ (C=0.1 in chloroform)) was dissolved in a mixture of chloroform (59 ml), carbon tetrachloride (130 ml) and water (118 ml) while heating. Azobisisobutyronitrile (300 mg) and bromine (1.24 g) were added thereto in order. The resultant mixture was heated under reflux for 1 hour. From the reaction mixture, an organic phase was separated, washed with aqueous sodium hyposulfite solution and water, dried over anhydrous sodium sulfate and concentrated to give the crude product of 7-bromo-9(S)-(1,1-ethylenedioxy)ethyl-6,9,11-trihydroxy-5,7,8,9,10,12-hexahydronaphthacene-5,12-dione as a red powder. This product was used in the subsequent step without purification.

(2) 7-Bromo-9(S)-(1,1-ethylenedioxy)ethyl-6,9,11-trihydroxy-5,7,8,9,10,12-hexahydronaphthacene-5,12-dione (500 mg) prepared in the foregoing step was reacted with N,N-dimethylethylenediamine (5 ml) in the same manner as in Example 1 (2). The resultant mixture was subjected to post-treatment to give the following products:

7(S)-(2-Dimethylaminoethyl)amino-9(S)-(1,1-ethylenedioxy)ethyl-6,9,11-trihydroxy-5,7,8,9,10,12-hexahydronaphthacene-5,12-dione as orange crystals. M.P., 165°–169° C. $[\alpha]_D^{20} +120°$ (C=0.1 in chloroform).

NMR (CDCl$_3$) δ: 1.5 (3H, s), 2.25 (6H, s), 2.00–3.15 (8H, m), 4.05 (4H, s), 4.25 (1H, brs, $\nu_{\frac{1}{2}}=8.3$ Hz), 7.65–7.90 (2H, m), 8.06–8.37 (2H, m). Mass spectrum: 483 (M+1)$^+$.

7(R)-(2-Dimethylaminoethyl)amino-9(S)-(1,1-ethylenedioxy)ethyl-6,9,11-trihydroxy-5,7,8,9,10,12-hexahydroxynaphthacene-5,12-dione as a brown semisolid. $[\alpha]_D^{20} -316°$ (C=0.1 in chloroform).

NMR (CDCl$_3$) δ: 1.45 (3H, s), 1.60–3.37 (9H, m), 2.18 (6H, s), 4.07 (4H, s), 4.47 (brt, J$_1$=J$_2$=9 Hz, $\nu_{\frac{1}{2}}=20.1$ Hz), 7.78 (2H, m), 8.29 (2H, m). Mass spectrum: 483 (M+1)$^+$.

EXAMPLE 8

In the same manner as in Example 3, 7(S)-(2-dimethylaminoethyl)amino-9(S)-(1,1-ethylenedioxy)ethyl-6,9,11-trihydroxy-5,7,8,9,10,12-hexahydronaphthacene-5,12-dione prepared in Example 7 was subjected to reaction and post-treatment to give 9(S)-acetyl-7(S)-(2-dimethylaminoethyl)amino-6,9,11-trihydroxy-5,7,8,9,10,12-hexahydronaphthacene-5,12-dione as orange crystals. M.P., 116°–120° C. $[\alpha]_D^{20} +160°$ (C=0.11 in chloroform).

NMR (CDCl$_3$) δ: 1.15–1.88 (2H, m), 2.26 (6H, s), 2.41 (3H, s), 2.13–3.32 (8H, m), 4.27 (1H, brs), 7.65–7.92 (2H, m), 8.08–8.38 (2H, m).

Hydrochloride, M.P., 218°–221° C.

REFERENCE EXAMPLE 1

A mixture of 7-deoxydaunomycinone (239 mg) (prepared from daunomycin hydrochloride according to the method as described in J. Org. Chem., 42, 3657 (1977)), benzene (15 ml), ethylene glycol (0.5 ml) and p-toluenesulfonic acid (10 mg) was heated under reflux for 3 hours, during which the by-produced water was eliminated from the reaction system. After cooling, the precipitated orange crystals of 7-deoxydaunomycinone-13-ethyleneacetal (M.P., 279°–282° C.) were collected by filtration.

EXAMPLE 9

(1) A mixture of 7-deoxydaunomycinone-13-ethyleneacetal (340 mg) prepared in Reference Example 1, chloroform (15 ml), carbon tetrachloride (30 ml) and water (20 ml) was heated under reflux, and a solution of bromine (300 mg) in carbon tetrachloride (4 ml) was dropwise added thereto. A half portion of 72 mg of azobisisobutyronitrile and the remainder were added to the reaction system respectively at the initial stage and at the final stage. After the dropwise addition was completed, heating under reflux was continued for 30 minutes. The reaction mixture was cooled to room temperature, and the organic phase was separated, washed with dilute sodium hyposulfite solution and water in order, dried over anhydrous sodium sulfate and concentrated under reduced pressure to give 7-bromo-7-deoxydaunomycinone-13-ethyleneacetal as red crystals. This product was used as such in the subsequent step without purification.

(2) In the same manner as in Example 1 (2), 7-bromo-7-deoxydaunomycinone-13-ethyleneacetal (100 mg) prepared in the foregoing step and N,N-dimethylethylenediamine (5 ml) were subjected to reaction and post-treatment. The product was purified by thin layer chromatography using silica gel and a mixture of dichloromethane and methanol (9:1) as an eluting solvent to give 7-deoxy-7-(2-dimethylaminoethyl)aminodaunomycinone-13-ethyleneacetal as orange crystals. M.P., 185°–188° C.

NMR (CDCl$_3$) δ: 1.35–1.78 (1H, m), 1.49 (3H, s), 2.07–3.42 (10H, m), 2.21 (3H, s), 4.07 (4H, brs), 4.33 (1H, brs), 7.40 (1H, brs), 7.65–7.88 (1H, m), 7.95–8.15 (1H, m). Mass spectrum: 513 (M+1)$^+$.

EXAMPLE 10

7-Deoxy-7(S)-(2-dimethylaminoethyl)aminodaunomycinone-13-ethyleneacetal (60 mg) prepared in Example 9 (2) was dissolved in a mixture of acetone (60 ml) and conc. hydrochloric acid (30 ml), and the resultant mixture was stirred at room temperature for 5 hours. After removal of the acetone by distillation under reduced pressure, the residue was adjusted to pH 8.0 and extracted with chloroform. The extract was dried and concentrated under reduced pressure to give 7-deoxy-7(S)-(2-dimethylaminoethyl)aminodaunomycinone as an orange solid.

NMR (CDCl$_3$) δ: 1.57–1.87 (1H, m), 2.11–3.33 (7H, m), 2.22 (6H, s), 2.38 (3H, s), 4.03 (3H, s), 4.29 (1H, brs), 7.31–8.02 (3H, m). Mass spectrum: 469 (M+1)$^+$.

REFERENCE EXAMPLE 2

(1) A mixture of 7-deoxydaunomycine (1.06 g) (prepared from daunomycin hydrochloride by the method as described in J. Org. Chem., 42, 3657 (1977)), dry dichloromethane (110.8 ml) and anhydrous aluminum chloride (3.32 g) was heated under reflux for 2 hours. The reaction mixture was dropwise added to a cold solution of oxalic acid (1.7 g) in water (60 ml). The resultant mixture was stirred at room temperature for 1 hour. The organic phase was separated, washed with water, dried over anhydrous sodium sulfate and concentrated under reduced pressure to give 7-deoxycarminomycinone as red brown crystals. M.P., 247°–249° C.

IR (Nujol) $\nu$ cm$^{-1}$: 3480, 1700, 1620, 1600. NMR (CDCl$_3$) δ: 1.7–2.0 (2H, m), 2.2 (3H, s), 2.7–3.0 (4H, m), 7.15–7.4 (1H, m), 7.5–7.95 (2H, m), 11.8–12.3 (1H, m), 12.3–12.7 (1H, m), 13.3–13.6 (1H, m). Mass spectrum: 368 (M+1)$^+$.

(2) A mixture of 7-deoxycarminomycinone (500 mg) prepared in the foregoing step, dry benzene (24 ml), ethylene glycol (0.72 ml) and p-toluenesulfonic acid (24 mg) was heated under reflux for 4 hours, during which the by-produced water was eliminated from the reaction system. After cooling, the precipitated orange crystals of 7-deoxycarminomycinone-13-ethyleneacetal were collected by filtration. M.P., 257°–259° C.

IR (Nujol) $\nu$ cm$^{-1}$: 3440, 1600, 1570. NMR (CDCl$_3$) δ: 1.45 (3H, s), 1.85–2.15 (2H, m), 2.65–3.15 (4H, m), 4.08 (4H, s), 7.2–8.0 (3H, m). Mass spectrum: 412 (M+1)$^+$.

EXAMPLE 11

(1) 7-Deoxycarminomycinone-13-ethyleneacetal (270 mg) prepared in Reference Example 2 was dissolved in dry carbon tetrachloride (1080 ml), and a solution of bromine (230 mg) in carbon tetrachloride (10 ml) was dropwise added thereto. A half portion of 28.35 mg of azobisisobutyronitrile and the remainder were added to the reaction mixture respectively at the initial stage and at the final stage. After the dropwise addition was completed, the reaction mixture was heated under reflux for 1 hour. The solvent was removed by distillation under reduced pressure to give 7-bromo-7-deoxycarminomycinone-13-ethyleneacetal as red brown crystals. This product was used as such in the subsequent step without purification.

(2) 7-Bromo-7-deoxycarminomycinone-13-ethyleneacetal (310 mg) prepared in the foregoing step and N,N-dimethylethylenediamine (10 ml) were subjected to reaction at −40° to −50° C. in a nitrogen stream for 1 hour. Excess of the amine was eliminated by distillation under reduced pressure. The residue was poured into ice water, adjusted to pH 8.0 and extracted with dichloromethane. The extract was concentrated and purified by silica gel chromatography using a mixture of dichloromethane and methanol (9:1) as an eluting solvent to give 7-deoxy-7(S)-(2-dimethylaminoethyl)aminocarminomycinone-13-ethyleneacetal as orange crystals. M.P., 151°–153° C.

IR (Nujol) $\nu$ cm$^{-1}$: 3100–3350, 1605, 1580. NMR (CDCl$_3$) δ: 1.45 (3H, s), 1.50–1.66 (1H, m), 2.2 (6H, s), 2.0–3.2 (8H, m), 4.05 (4H, s), 4.2–4.35 (1H, m, $\nu\frac{1}{2}$=7.5 Hz), 7.5–7.9 (3H, m). Mass spectrum: 500 (M+2)$^+$.

EXAMPLE 12

7-Deoxy-7(S)-(2-dimethylaminoethyl)aminocarminomycinone-13-ethyleneacetal (55 mg) prepared in Example 11 (2) was dissolved in a mixture of acetone (55 ml) and conc. hydrochloric acid (22 ml), and the resultant mixture was stirred at room temperature for 16 hours. After removal of the acetone by distillation under reduced pressure, the residue was washed with dichloromethane and adjusted to pH 8.0. The product was extracted with dichloromethane, and the extract was dried over anhydrous sodium sulfate and concentrated to give 7-deoxy-7(S)-(2-dimethylaminoethyl)aminocarminomycinone as orange crystals. M.P., 244°–246° C.

IR (Nujol) $\nu$ cm$^{-1}$: 3100–3500, 1718, 1600. NMR (CDCl$_3$) δ: 1.6–1.78 (1H, m), 2.21 (6H, s), 2.38 (3H, s), 2.0–2.1 (8H, m), 4.1–4.3 (1H, m, $\nu\frac{1}{2}$=9 Hz), 7.1–7.8 (3H, m). Mass spectrum: 454 (M+1)$^+$.

Hydrochloride, M.P., 155°–157° C.

EXAMPLE 13

(1) A mixture of 9-(1,1-ethylenedioxy)ethyl-6,9-dihydroxy-5,7,8,9,10,12-hexahydronaphthacene-5,12-dione (657 mg), chloroform (33 ml), carbon tetrachloride (13 ml) and water (26 ml) was stirred at room temperature, and bromine (530 mg) and azobisisobutyronitrile (130 mg) were added thereto, and the resulting mixture was stirred at the same temperature as above for 1 hour. From the reaction mixture, the organic phase was separated, washed with water, dried over anhydrous sodium sulfate and concentrated. The residue was crystallized from ether to give 7-bromo-9-(1,1-ethylenedioxy)ethyl-6,9-dihydroxy-5,7,8,9,10,12-hexahydronaphthacene-5,12-dione (576 mg). M.P., 173°–176° C.

IR (Nujol) $\nu$ cm$^{-1}$: 3475, 1670, 1630, 1590.

(2) 7-Bromo-9-(1,1-ethylenedioxy)ethyl-6,9-dihydroxy-5,7,8,9,10,12-hexahydronaphthacene-5,12-dione (571 mg) prepared in the foregoing step and N,N-dimethylethylenediamine (10 ml) were subjected to reaction in a nitrogen stream while cooling with ice for 1 hour. Excess of the N,N-dimethylethylenediamine was eliminated by distillation under reduced pressure. The residue was dissolved in dichloromethane (2 ml) and ether (4 ml) was added thereto, whereby 7-(2-dimethylaminoethyl)amino-9-(1,1-ethylenedioxy)ethyl-6,9-dihydroxy-5,7,8,9,10,12-hexahydronaphthacene-5,12-dione was obtained as yellow crystals (124 mg). M.P., 192°–196° C.

IR (Nujol) $\nu$ cm$^{-1}$: 1670, 1630, 1590, 1575. NMR (CDCl$_3$) δ: 1.44 (3H, s), 1.62–3.05 (6H, m), 2.24 (6H, s), 3.13 (2H, bs), 4.03 (4H, bs), 4.32 (1H, bs), 7.60 (1H, s), 7.75 (2H, m), 8.27 (2H, m).

EXAMPLE 14

7-(2-Dimethylaminoethyl)amino-9-(1,1-ethylenedioxy)ethyl-6,9-dihydroxy-5,7,8,9,10,12-hexahydronaphthacene-5,12-dione (60 mg) prepared in Example 13 (2) was added to a mixture of acetone (60 ml) and conc. hydrochloric acid (24 ml), and the resultant mixture was heated under reflux for 1 hour. After removal of acetone by distillation under reduced pressure, the water layer was washed with dichloromethane, adjusted to pH 8.0 with aqueous sodium hydroxide solution and extracted with dichloromethane. The extract was purified by silica gel chromatography using a mixture of chloroform and methanol (9:1) to give 7-(2-dimethylaminoethyl)amino-9-acetyl-6,9-dihydroxy-5,7,8,9,10,12-hexahydronaphthacene-5,12-dione (55 mg). M.P., 170°–172° C.

IR (Nujol) $\nu$ cm$^{-1}$: 3300, 1715, 1675, 1630, 1595, 1575. NMR (CDCl$_3$) δ: 1.60–3.28 (9H, m), 3.23 (6H, s), 2.39 (3H, s), 4.32 (1H, bs), 7.47 (1H, s), 7.75 (2H, m), 8.23 (2H, s).

Hydrochloride, M.P., 207°–216° C.

What is claimed is:

1. A (7S,9S) isomer or its racemic modification of the aminonaphthacene derivative of the formula:

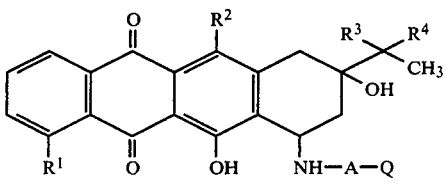

wherein $R^1$ is a hydrogen atom, a hydroxyl group or a lower alkoxy group, $R^2$ is a hydrogen atom or a hydroxyl group, $R^3$ and $R^4$ are each a lower alkoxy group or, when taken together, represent an ethylenedioxy group or an oxo group, A is an ethylene group optionally bearing at least one lower alkyl and Q is a hydroxyl group, a lower alkoxy group or a dimethylamino group, or an acid addition salt thereof.

2. The (7S,9S) isomer or its racemic modification according to claim 1, wherein $R^3$ and $R^4$ are each a lower alkoxy group or, when taken together, represent an ethylenedioxy group.

3. The (7S,9S) isomer or its racemic modification according to claim 1, wherein $R^3$ and $R^4$ are taken together to represent an oxo group.

4. The (7S,9S) isomer or its racemic modification according to claim 3, wherein $R^1$ is a hydrogen atom and $R^2$ is a hydroxyl group.

5. The (7S,9S) isomer or its racemic modification according to claim 3, wherein $R^1$ and $R^2$ are each a hydroxyl group.

6. A (7S,9S) isomer or its racemic modification of 7-(2-dimethylaminoethyl)amino-9-acetyl-6,9,11-trihydroxy-5,7,8,9,10,12-hexahydronaphthacene-5,12-dione.

7. A (7S,9S) isomer or its racemic modification of 7-(2-hydroxyethyl)amino-9-acetyl-6,9,11-trihydroxy-5,7,8,9,10,12-hexahydronaphthacene-5,12-dione.

8. A (7S,9S) isomer or its racemic modification of 7-(2-methoxyethyl)amino-9-acetyl-6,9,11-trihydroxy-5,7,8,9,10,12-hexahydronaphthacene-5,12-dione.

9. A (7S,9S) isomer or its racemic modification of 7-(2-hydroxypropyl)amino-9-acetyl-6,9,11-trihydroxy-5,7,8,9,10,12-hexahydronaphthacene-5,12-dione.

10. An anti-tumor composition in the form of a solid or liquid pharmaceutical preparation, said composition containing an effective anti-tumor amount of a compound according to claim 1 as an active ingredient.

* * * * *